United States Patent [19]

Gupta

[11] 4,300,386

[45] Nov. 17, 1981

[54] POROSIMETER ARRANGEMENT

[76] Inventor: Krishna M. Gupta, 18-B Morningside Manor, Ithaca, N.Y. 14850

[21] Appl. No.: 111,601

[22] Filed: Jan. 14, 1980

[51] Int. Cl.³ .............................................. G01N 15/08
[52] U.S. Cl. .................................................... 73/38
[58] Field of Search ............................................ 73/38

[56] References Cited

U.S. PATENT DOCUMENTS

| | | | |
|---|---|---|---|
| 2,537,668 | 1/1951 | Hebard | 73/38 |
| 3,882,714 | 5/1975 | Libal et al. | 73/38 |

FOREIGN PATENT DOCUMENTS 326491   4/1972   U.S.S.R. .................................. 73/38

OTHER PUBLICATIONS

Baker, D. J., *A Low-pressure Mercury Porosimeter*, In Journ. of Phys. E Sci. Instr., vol. 4, 1971, pp. 388–389.

*Primary Examiner*—Jerry W. Myracle
*Assistant Examiner*—Joseph W. Roskos
*Attorney, Agent, or Firm*—Karl F. Milde, Jr.

[57] ABSTRACT

A mercury instrusion type porosimeter arrangement wherein a vessel containing the mercury used for intrusion is disposed such that a conduit issuing therefrom extends downwardly to enable mercury to flow through the action of gravity. The conduit extends to a chamber which contains the sample of material whose porosity characteristics are to be determined and to the tube of a penetrometer assembly which contains the mercury whose height is to be measured, the penetrometer assembly comprising a tube and an electrically actuated transducer associated therewith which senses the height of the mercury in the tube. With this arrangement, there is eliminated the need to introduce atmospheric pressure to force mercury into the penetrometer tube, thus eliminating an initial pressure error. There is, thereby, enabled the precise measurement of the porosity characteristics of materials with larger pores, heretofore unattainable.

17 Claims, 2 Drawing Figures

POROSIMETER ARRANGEMENT

BACKGROUND OF THE INVENTION

1. Field of the Invention

This invention relates to porosimetry which is the measurement of the porosity characteristics of materials. More particularly, it relates to porosimeters of the mercury intrusion type.

2. Description of the Prior Art

In mercury intrusion porosimeters, mercury which is a non-wetting cohesive liquid, is forced into the pores of a sample of a charge of a material whose porosity is to be determined and the volume of the amount of mercury caused, in this manner, to permeate the sample charge and the pressure at which it is so caused, is measured. The results of such measurement can then be used to determine porosity characteristics of the material, such characteristics being, for example, pore volume, pore size distribution, surface area, absolute particle density and complexity or pores.

In the patent application of Krishna M. Gupta for Porosimeter, Ser. No. 917,347, filed June 20, 1978, and now U.S. Pat. No. 4,203,317, there is disclosed an efficacious porosimeter of the mercury intrusion type. The disclosure of patent application, Ser. No. 917,347, is hereby incorporated by reference into this patent application.

The porosimeter disclosed in patent application Ser. No. 917,347, essentially comprises a sample chamber, a tube disposed over the chamber and communicating therewith, a differential transformer type transducer disposed around the tube, a mercury source, and means for evacuating and thereafter introducing pressure into the arrangement. This porosimeter structure consists of components which are rugged, being made of a material such as stainless steel, and are constructed such that they can be placed in pressure tight relationship.

In the operation of this porosimeter, a weighed sample charge of a material whose porosity characteristics are to be determined is first placed into the sample chamber. The structure are then all made pressure-tight and the system is evacuated to as near a vacuum as is possible. Mercury is now permitted to flow to fill the sample chamber and air is then carefully introduced into the system to force mercury into the tube to fill it with mercury to a desired operating height. The tube contains a ferromagnetic body which has a specific gravity such that it floats in the mercury, and is suitably of a right circular cylindrical configuration, this body operating as the movable core of the differential transformer. After the tube has been filled with mercury to a position where the core is positioned to give a desired initial pre-reading on a voltmeter connected to the transformer, pressure is applied to the mercury in the tube and the chamber by the introduction of further air pressure into the system, and, if required, by added pressure generating means to cause the mercury to as completely as possible intrude into and permeate the sample. As a result of such pressure application, the height of the mercury in the tube is caused to drop. The resulting new height of the mercury is sensed by the transducer and recorded on the voltmeter. In this manner, the volume of the mercury intruded into the sample is obtained. The value of this volume and the value of the pressure applied, enable the determination of the various porosity characteristics of the sample as has been mentioned hereinabove.

As has been stated, the porosimeter disclosed in patent application, Ser. No. 917,347, is generally quite effective for the purposes to which it is put. However, the results obtained with it when the porosity characteristics of a material having relatively large pores is being determined are not as precise as in the case where the material has smaller pores. To understand the reason for this imprecision, it is to be realized that the larger the pores, the less resistance there is to the intrusion thereinto of mercury. Therefore, whereas a small pore material may require great amounts of pressure to force mercury therethroughout, comparatively little pressure may be required to permeate with mercury a material having relatively large pores.

Thus, in the operation of this porosimeter, when air pressure is first introduced into the evacuated system to force the mercury into the tube, this small amount of pressure on the mercury has a negligible effect on the precision of the finally attained mercury volume in the case where a small pore material is being examined, since little if any mercury will be forced into its pores. However, where the material has relatively large pores, this small amount of pressure that has to be introduced to force the mercury into the tube can cause a large enough amount of mercury to enter the material sample so as to render the final results less precise than desired. Ideally, any imprecision so introduced can be eliminated if such pressure is used only to cause mercury to intrude into the sample and no portion thereof has to be initially used to fill the tube.

Accordingly, it is an important object of this invention to provide a porosimeter arrangement of the type disclosed in patent application, Ser. No. 917,347, wherein the porosity characteristics of materials can be precisely determined irrespective of the size of the pores.

It is another object to provide a porosimeter arrangement in accordance with the preceding object wherein pressure is employed essentially only to cause mercury to intrude into the sample of the material whose porosity characteristics are being determined.

It is a further object to provide a porosimeter assembly in accordance with the preceding objects wherein there is enabled the concurrent porosity determination of a plurality of samples.

SUMMARY OF THE INVENTION

Generally speaking, and in accordance with the invention, there is provided a porosimeter arrangement which includes a chamber for containing a sample of a material whose porosity characteristics are to be determined, a penetrometer assembly comprising a tube communicating with the sample chamber and an electrically actuated transducer associated with the tube for sensing the height of a non-wetting fluid such as mercury in the tube, and a source of the fluid. The fluid source is a vessel disposed such that a conduit extends therefrom downwardly and is connected to the sample chamber and the tube. This disposition permits the fluid to flow by the action of gravity through the conduit to fill the chamber and the tube with the fluid. The arrangement further includes means adapted to be connected to the vessel, the chamber, and the tube for the arrangement's evacuation, and means adapted for connection thereto to introduce atmospheric pressure into the arrangement. Reservoir means is provided adapted to be connected to the tube and the chamber, to drain the fluid therefrom at the conclusion of a test. Auxiliary pressure generating means may be included for providing pressure to the top of the mercury column in the tube, the auxiliary pressure generating means comprising a vessel containing an incompressible fluid, (such as isopropyl alcohol), and having a lower specific gravity than the intrusion fluid, a conduit connected between the last-named vessel and the top of the tube for introducing a small portion of this incompressible fluid to the top of the intrusion fluid, a pressure generator, and means for connecting the pressure generator to the tube to apply pressure to the intrusion fluid through the incompressible fluid.

Also, and in accordance with the invention, there is provided a porosimeter assembly. The assembly comprises a plurality of units having a sample chamber and penetrometer assembly as described hereinabove, in connection with the porosimeter arrangement, and single evacuating, atmospheric pressure introduction, reservoir, and pressure generating means. In this assembly, each unit operates as described hereinabove in connection with the description of the porosimeter arrangement. Thus, fluid flows from the intrusion fluid containing vessel by the action of gravity to fill concurrently the tubes and chambers of all of the units. All of the assembly is evacuated with the application of vacuum, and atmospheric pressure is also introduced throughout the assembly when it is applied. The single reservoir means is adapted to be connected to all of the tubes and chambers to concurrently drain the whole assembly of intrusion fluid. The single auxiliary generating means, when connected, applies pressure to all of the tubes of the assembly. With this assembly, there is enabled the concurrent determination of the porosity characteristics of a plurality of samples.

For a better understanding of the invention, together with other and further objects thereof, reference is made to the following description taken in conjunction with the accompanying drawing.

DESCRIPTION OF THE EMBODIMENTS

Figure 1:
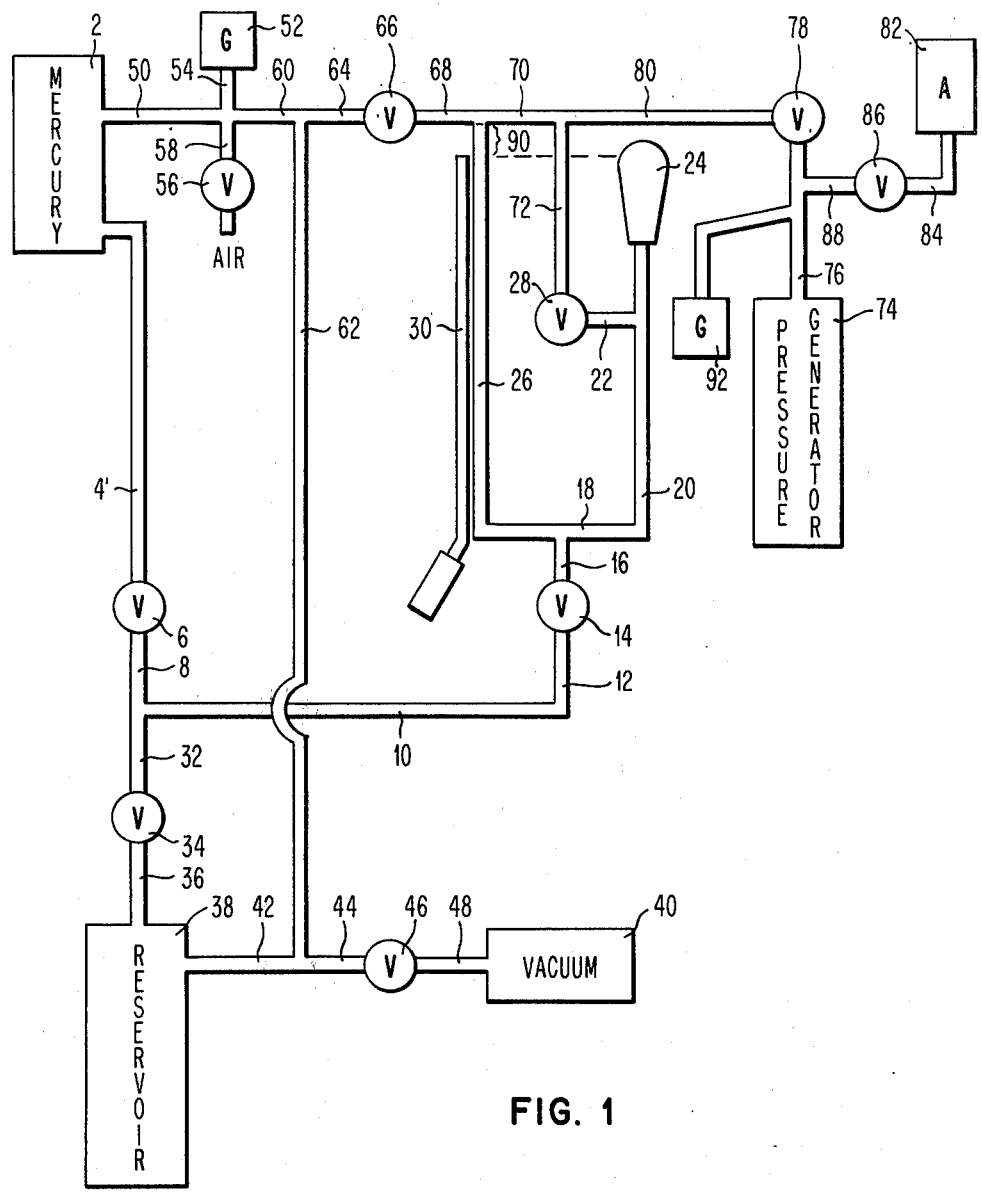
FIG. 1 is a diagrammatic representation of an illustrative embodiment of a porosimeter arrangement constructed in accordance with the principles of the invention.

Referring now to FIG. 1, a vessel 2 containing mercury is disposed such that a conduit 4 leading from the bottom or near the bottom thereof can convey mercury, when a valve 6 is opened, to the tube and sample chamber of the system. Conduit 4 extends downwardly from vessel 2 and, with valve 6 open, mercury is caused to flow by the action of gravity. The spatial disposition of the structures is such that the degree of gravity provided is sufficient to readily enable the filling of the tube and sample chamber with mercury.

Conduits 8, 10, and 12 extend to a relatively high pressure valve 14, a conduit 16 extending from valve 12 and leading into conduits 18, 20 and 22. Conduit 20 terminates in a sample chamber 24 wherein a weighed sample of the material whose porosity characteristics are to be determined is introduced.

Conduit 18 also extends to a tube 26 which is filled, during the filling process, with mercury to a height equal to the height of mercury in the mercury filled sample chamber 24. Conduit 22 extends to a relatively high pressure valve 28. The structure 30 shown closely adjacent to tube 26 is intended to depict a transducer such as disclosed in the above-referred to patent application, Ser. No. 917,347, i.e., the differential transformer and the operatively associated ferromagnetic float within the mercury containing tube. The combination of tube 26 and transducer 30 is suitably termed a penetrometer assembly and, hereinafter, this combination will be so termed.

Extending from the junctions of conduits 8 and 10 is a conduit 32 which extends to a relatively low pressure valve 34, a conduit 36 extending from valve 34 to a reservoir 38. Reservoir 38 is connected to a stage 40 legended vacuum, stage 40 being intended to depict evacuating apparatus such as a vacuum pump. This connection is through a conduit 42, a conduit 44, a relatively low pressure valve 46 and a conduit 48. A conduit 50 extends from mercury vessel 2 to an air pressure guage 52 via a conduit 54 and to a relatively low pressure valve 56 through a conduit 58. Valve 56, when opened, introduces air or other gases into the system from the exterior. Extending from the junctions of conduits 54 and 58 is a conduit 60, a conduit 62 being interposed between conduit 60 and the junctions of conduits 42 and 44.

A conduit 64 extends from the junction of conduits 60 and 62 to a relatively high pressure valve 66, a conduit 68 extending from valve 66 to tube 26. A conduit 70 extends from the junction of conduit 68 and tube 26 to a conduit 72 which extends from valve 28.

A stage 74, legended pressure generator, is intended to depict a pressure generator such as referred to in the above-mentioned patent application Ser. No. 917,347, i.e., a device of the type which operates in conjunction with an incompressible fluid. A conduit 76 extends from pressure generator 74 to a high pressure valve 78, a conduit 80 extending from valve 78 to the junction of conduits 70 and 72. The box 82, legended A, is intended to depict a vessel containing such incompressible fluid. A conduit 84 extends from vessel 82 to a relatively low pressure valve 86, a conduit 88 extending from valve 86 to conduit 76.

In considering the operation of the arrangement shown in FIG. 1, a weighed sample is inserted into chamber 24. Then with valves 56, 6, 34 and 78 closed and the other valves opened, the evacuating apparatus of vacuum 40 is actuated to exhaust the system down to as near vacuum conditions as is possible. With both the mercury vessel 2 and the remainder of the arrangement connected for evacuation and valve 6 closed to prevent flow of mercury, there results the situation wherein there is no differential pressure between sample chamber 24 and the mercury vessel 2.

After evacuation is completed, valve 34 is closed and valve 6 is opened whereby mercury is permitted to flow by the action of gravity from vessel 2, through conduit 4, valve 6, conduits 8, 10, 12, valve 14, and conduits 16, 18 and 20 into chamber 24 and tube 26 until chamber 24 and tube 26 are filled to the desired level. Valve 6 is now closed and, at this juncture, the net pressure on the mercury in and surrounding the sample results from the head difference between tube 26 and sample chamber 24. This height difference can be controlled during the filling process down to close to zero thereby enabling great flexibility in the testing of materials of different and relatively large sized pores. The height difference which can be controlled is designated with the numeral 90.

In any event, it is seen that even without the capability of initially providing almost zero head difference pressure on the sample, no external pressure has been introduced into the system and consequently on the mercury in the sample because tube 26 has been filled only through the action of gravity. This is to be distinguished from the arrangement shown in patent application, Ser. No. 917,347, wherein, some atmospheric pressure has to be introduced to force fluid into the penetrometer tube.

After the filling step has been completed, valves 14 and 28 are closed and with evacuating apparatus 40 disconnected, valve 56 is manipulated carefully to enable atmospheric pressure to enter conduit 58 in increments, as monitored on guage 52, the pressure being applied to the sample in chamber 24 through conduits 60 and 64, valve 66, conduit 68, and through the mercury column in tube 26. As a result of the application of this pressure, the mercury is forced to intrude into the sample in chamber 24 with a resulting drop in the height of the mercury in tube 26. The transducer 30 senses this new height of the mercury column in the same manner as the operation of the penetrometer assembly in patent application, Ser. No. 917,347. This sensed information is suitably read out on a voltmeter (not shown) which is associated with the transducer. The readings taken during the testing of a sample from the voltmeter and from pressure guage 52 provide the information for determining the porosity characteristics of the new sample.

As has been mentioned, the ease of intrusion of the mercury into the pores of the sample varies inversely as the size of the pores. Clearly with valve 56 fully opened, the system can only be brought to a maximum pressure of one atmosphere. Since much greater pressures may be required to totally intrude mercury into a material with quite small pores, means are provided for producing pressures on the mercury in the sample greatly exceeding one atmosphere. To this end, there is provided a pressure generator 74 which is of the same type as the pressure generator disclosed in patent application, Ser. No. 917,347. Vessel 82 contains an incompressible liquid such as isopropyl alcohol, the characteristics required of the liquid in vessel 82 being that it be incompressible, and lighter than the ferromagnetic float of transducer 30 whereby the float sinks therein but floats in the mercury in the tube 26. Thus, when higher pressures are required to effect complete intrusion, with valves 86 and 78 open, and valve 28 and 66 closed, some fluid is introduced from vessel 82 into the top of the mercury in tube 26 through conduit 84, conduit 88, valve 78, conduit 80 and conduit 70. The valve 86 is then closed and the pressure generator 74 is now operated. The resulting readings are taken from the voltmeter which shows changes in mercury height in tube 26, and from a pressure guage 92 associated with pressure generator 74.

After a testing of a sample is complete, valve 34 is opened, and with valve 14 also opened, the mercury is drained out of tube 26 and chamber 24 by the action of gravity through conduits 20, 18 and 16, valve 14, conduits 12, 10 and 32, valve 34 and conduit 36.

Figure 2:
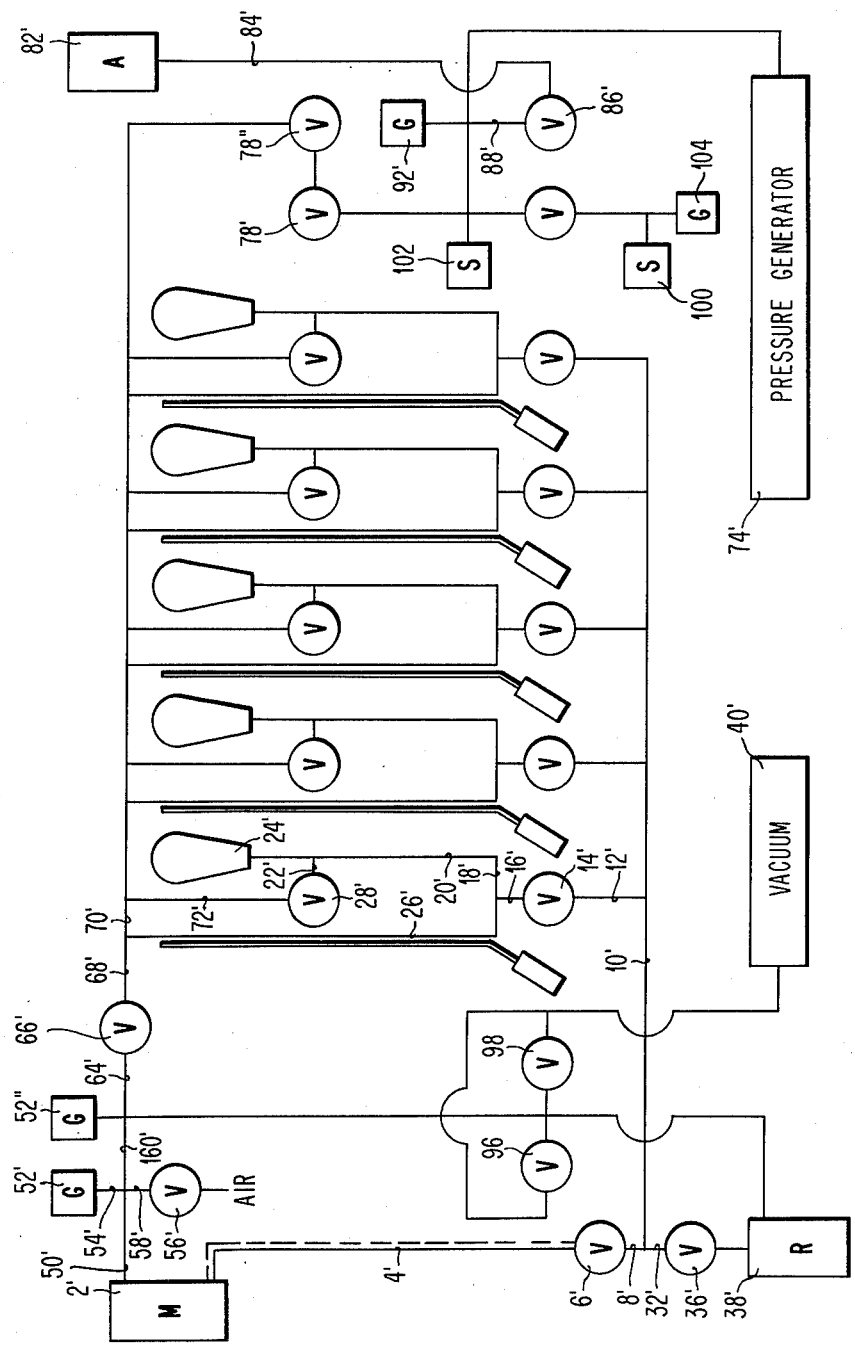
FIG. 2 is a schematic depiction of a porosimeter assembly for concurrently utilizing a plurality of the porosimeter arrangements, shown in FIG. 1.

Referring now to the embodiment of the porosimeter assembly according to the invention shown in FIG. 2 wherein a plurality of samples can be concurrently tested, the individual operating units thereof are essentially the same as the arrangement shown in FIG. 1. Accordingly, like structures bear the same designating numerals but with the prime notation. For convenience of explication, only one operating unit has been numerically designated.

In the system shown in FIG. 2, the mercury vessel 2' and legended M supplies mercury for all of the units in the system. Similarly, the reservoir 38' and legended R drains the whole system. The air valve 56' is the common source of atmospheric pressure for the total system and, in a like manner, vacuum state 40' and pressure generator 74' respectively provide evacuation and auxiliary pressure to the system. Vessel 82' is a common system source of the incompressible fluid such as isopropyl alcohol. Valves 96 and 98 are provided as shown in the evacuating circuit, valve 96 acting to slow the action of the evacuating apparatus in a situation where the sample may be of a powder that could be sucked out of a sample chamber during evacuation. Valve 98, by contrast, may be one that permits relatively fast evacuation. The boxes 100 and 102 legended S are associated with the pressure generator and are intended to depict safety rupture disks. A low pressure guage 104, legended G, is conveniently provided in association with disk 100, guage 92' being a high pressure guage.

The operation of the multiple unit of FIG. 2 is essentially a parallel summation of the operations of the single units, each single unit operating as the single unit of FIG. 1. Thus, after as many as desired of the sample chambers 24' are loaded with samples to be tested, the system is evacuated, and then the penetrometer tubes and sample chambers are filled with mercury through open valve 6'. Thereafter, valve 56' is manipulated and pressure generator 74' is operated as needed, to provide the necessary test information, the information being obtained from the voltmeters associated with the penetrometer assemblies and the pressure guages 52', 92' and 104. While the invention has been described hereinabove in terms of two illustrative embodiments thereof, the invention itself is not limited thereto, but rather comprehends all modifications of, and departures from those embodiments properly falling within the spirit and scope of the appended claims.

What is claimed is:

1. A porosimeter arrangement comprising, in combination, (a) a sample chamber having a first conduit extending downwardly therefrom; (b) a penetrometer tube arranged upright at substantially the same elevation as said sample chamber, said penetrometer tube communicating at its lower end with said first conduit; (c) a vessel containing a non-wettable sample intrusion fluid arranged at at least the same elevation as said sample chamber; and (d) a second conduit extending downwardly from said vessel and communicating with said penetrometer tube and said first conduit to enable said fluid to flow by gravity from said vessel to said tube and said chamber.

2. In a porosimeter arrangement as defined in claim 1 and further including evacuating means adapted to be connected to said vessel, said tube and said chamber to evacuate said arrangement.

3. In a porosimeter arrangement as defined in claim 2 and further including means adapted to be connected to said arrangement to controllably introduce atmospheric pressure into said arrangement and to apply such pressure to said fluid in said chamber and said tube.

4. In a porosimeter arrangement as defined in claim 3 and further including pressure generating means adapted to be connected to apply pressure to said fluid when it is in said chamber and said tube.

5. In a porosimeter as defined in claim 4 wherein said fluid constitutes a first fluid and said vessel constitutes a first vessel and wherein said pressure generating means comprises:
   (a) a second vessel;
   (b) a second substantially incompressible fluid contained in said second vessel and having a specific gravity less than said first fluid;
   (c) means for introducing said second fluid to said tube on top of said first fluid in said tube; and
   (d) a pressure generator adapted to be connected to said arrangement to apply pressure to said first fluid through said second fluid.

6. In a porosimeter arrangement as defined in claim 5 wherein said transducer comprises a differential transformer adapted to be actuated by connection to a power source and which is disposed adjacent a section of said tube, and a ferromagnetic body floating on the top of said first fluid in said tube, said body functioning as the movable core of said transformer, said body moving in response to changes of height of said first fluid in said tube.

7. In a porosimeter arrangement as defined in claim 6 wherein said first and non-wetting intrusion fluid is mercury.

8. In a porosimeter arrangement as defined in claim 6 wherein said second and incompressible fluid is isopropyl alcohol.

9. In a porosimeter arrangement as defined in claim 6 and further including reservoir means adapted to be connected to said chamber and said tube to drain the fluid therefrom, said evacuating means also being adapted to be connected to said reservoir.

10. In a porosimeter arrangement as defined in claim 4, and further including second valve means arranged between the top of said penetrometer tube above the level of said chamber and the top of said vessel for preventing the application of pressure to said vessel.

11. In a porosimeter arrangement as defined in claim 10, wherein the top of said penetrometer tube is connected to a source of atmospheric pressure.

12. In a porosimeter arrangement as defined in claim 11, further including pressure generating means connected to the top of said penetrometer tube for applying superatmospheric pressure to said fluid.

13. In a porosimeter arrangement as defined in claim 1, and further including first valve means arranged in said second conduit for selectively preventing flow of said fluid in said second conduit.

14. A porosimeter assembly comprising: (a) a plurality of porosimeter arrangements, each of said arrangements including: (1) a chamber for containing a sample of a material whose porosity characteristics are to be determined, and (2) a penetrometer, said penetrometer including an upright tube arranged at substantially the same height as said chamber and communicating with the bottom of said chamber and an electrically actuated transducer operatively associated with said tube for sensing the height of a first and non-wetting intrusion fluid in said tube; (b) a vessel for containing said first fluid; (c) a conduit extending downwardly from said vessel and connected to said tubes and the bottom of said chambers in all of the porosimeter arrangements in said assembly to enable said first fluid to flow concurrently from said first vessel to all of said tubes and said chambers by the action of gravity; (d) evacuating means adapted to be connected concurrently to all of said porosimeter arrangements and said vessel to evacuate said porosimeter assembly; and (e) means adapted to be connected to said assembly to controllably introduce atmospheric pressure into said assembly.

15. A porosimeter assembly as defined in claim 14 and further including pressure generating means adapted to be connected to apply pressure to said first fluid when it is in said chambers and said tubes, said pressure generating means comprising:
   (a) a second vessel;
   (b) a second substantially incompressible fluid having a specific gravity less than said first fluid contained in said second vessel;
   (c) means communicating with said second vessel for introducing said second fluid into all of said tubes in said assembly on the tops of said first fluid in said tubes; and
   (d) a pressure generator adapted to be connected to said arrangement to apply pressure to said first fluid through said second fluid in said tubes.

16. A porosimeter assembly as defined in claim 14 and further including reservoir means adapted to be connected to all of said chambers and said tubes in said assembly to drain fluid therefrom, said evacuating means also being adapted to be connected to said reservoir.

17. A porosimeter assembly as defined in claim 16 wherein said first fluid is mercury and said second fluid is isopropyl alcohol.

* * * * *